United States Patent [19]
Härkönen et al.

[11] Patent Number: 6,037,379
[45] Date of Patent: Mar. 14, 2000

[54] SERUM CHOLESTEROL LOWERING AGENT

[75] Inventors: Pirkko Härkönen, Turku; Tatu Miettinen, Espoo; Eero Mäntylä, Piispanristi; Lauri Kangas, Raisio, all of Finland; Michael DeGregorio, Granite Bay, Calif.

[73] Assignee: Orion Corporation, Espoo, Finland

[21] Appl. No.: 09/142,321

[22] PCT Filed: Mar. 4, 1997

[86] PCT No.: PCT/FI97/00140

§ 371 Date: Oct. 8, 1998

§ 102(e) Date: Oct. 8, 1998

[87] PCT Pub. No.: WO97/32574

PCT Pub. Date: Sep. 12, 1997

[30] Foreign Application Priority Data

Mar. 4, 1996 [FI] Finland .................................. 9604577

[51] Int. Cl.$^7$ .................................................. A61K 31/40
[52] U.S. Cl. .............................................................. 514/721
[58] Field of Search ............................................... 514/721

[56] References Cited

U.S. PATENT DOCUMENTS 4,996,225  2/1991  Tiovola et al. .

OTHER PUBLICATIONS

CA 114:220854, Kangas, Cancer Chemother. Pharmacol, 27 (1), 8–12, 1990.
Drugnl AN 95:1133 R&D Focus Drug News, Jul. 10, 1995.
"Biochemical and Pharmacological Effects of Toremifene Metabolites", Lauri Kangas, Cancer Chemother Pharmacol, 1990, vol. 27, pp. 8–12.
"Tamoxifen and Toremifene Lower Serum Cholesterol by Inhibition of $\Delta^8$–Cholesterol Conversion to Lathosterol in Women with Breast Cancer" H. Gylling et al. Journal of Clinical Oncology, Dec. 1995; vol. 13, No. 12, pp. 2900–2905.
"Pharmacokinetics of Toremifene", M. Anttila et al., J. Steroid Biochemistry, 1990, vol. 36, No. 3, pp. 249–252.
"Metabolism of Toremifene in the Rat", H. Sipilä et al., J. Steroid Biochemistry, 1990, vol. 36, No. 3, pp. 211–215.
"In Vitro and In Vivo Binding of Toremifene and its Metabolites in Rat Uterus", N. Simberg et al. J. Steroid Biochemsitry, 1990, vol. 36, No. 3, pp. 197–202.
"Phase I Clinical and Pharmokinetics Study of High–Dose Toremifene in Postmenopausal Patients with Advanced Breast Cancer", James Bishop et al., Cancer Chemother Pharmacol, 1992, vol. 30, pp. 174–178.

*Primary Examiner*—Rebecca Cook
*Attorney, Agent, or Firm*—Burns, Doane, Swecker & Mathis, L.L.P.

[57] ABSTRACT

A method of lowering serum cholesterol levels comprising administering to a patient in need of such treatment an effective amount of Z-2-[4-(4-chloro-1,2-diphenyl-but-1-enyl)phenoxy]ethanol, as well as pharmaceutical compositions useful in the method, is disclosed.

6 Claims, No Drawings

SERUM CHOLESTEROL LOWERING AGENT

This is a 371 PCT/FI97/00140 filed Mar. 4, 1997

This invention relates to the use of Z-2-[4-(4-chloro-1,2-diphenyl-but-1-enyl)phenoxy]ethanol for lowering serum total or LDL cholesterol or increasing serum HDL cholesterol.

It has been demonstrated that elevated levels of serum cholesterol associated with low density lipoproteins (LDL) are a major contributing factor in the development and progression of atherosclerosis. Low serum HDL cholesterol is an independent risk factor for atherosclerosis. Therefore it is desirable to provide a method for reducing serum total cholesterol or LDL cholesterol levels combined with an increasing effect on HDL cholesterol levels in patients with hypercholesterolemia or at risk of developing hypercholesterolemia.

Z-2-[4-(4-chloro-1,2-diphenyl-but-1-enyl)phenoxy] ethanol, also known as (deaminohydroxy)toremifene, having the chemical structure represented by formula,

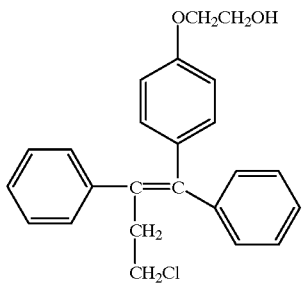

is a metabolite of known antiestrogen drug toremifene. Toremifene is currently used clinically for the treatment of estrogen receptor positive breast cancer.

Z-2-[4-(4-chloro-1,2-diphenyl-but-1-enyl)phenoxy] ethanol has been earlier described e.g. in Sipilä, H. et al., "Metabolism of toremifene in the rat", J. Steroid Biochem., 36, 3, 211–215, (1990), in Kangas, L., "Biochemical and pharmacological effects of toremifene metabolites", Cancer Chemother. Pharmacol., (1990), 27, 8–12, in Anttila, M. et al., "Pharmacokinetics of toremifene", J. Steroid Biochem., 36, 3, 249–252, (1990), in Simberg, N. et al, "In vitro and in vivo binding of toremifene and its metabolites in rat uterus", J. Steroid Biochem., 36, 3, 197–202, (1990), in Bishop, J. et al., "Phase I clinical and pharmacokinetics study of high dose toremifene in postmenopausal patients with advanced breast cancer", Cancer Chemother. Pharmacol., 30, 174–178 (1992) and in the applicant's International Patent Application No. PCT/FI95/00475. It was shown that this compound is active in producing the release of TGF-β but is devoid of significant hormonal activity.

Now it has been found that Z-2-[4-(4-chloro-1,2-diphenyl-but-1-enyl)-phenoxy]ethanol is active in lowering serum total and LDL cholesterol and increasing serum HDL cholesterol. Since this compound lack significant hormone associated side effects, it is especially suitable for lowering serum total or LDL cholesterol or increasing serum HDL cholesterol, as well as in the treatment or prevention of atherosclerosis.

The invention provides a method of lowering serum total or LDL cholesterol levels or increasing serum HDL cholesterol levels, which method comprises administering to a patient in need of such treatment an effective amount of Z-2-[4-(4-chloro-1,2-diphenyl-but-1-enyl)phenoxy]ethanol.

The invention also provides a method for the prevention or treatment of atherosclerosis, which method comprises administering to a patient in need of such treatment an effective amount of Z-2-[4-(4-chloro-1,2-diphenyl-but-1-enyl)phenoxy]ethanol.

The present invention also provides the use of Z-2-[4-(4-chloro-1,2-diphenyl-but-1-enyl)phenoxy]ethanol in the manufacture of a medicament for use in lowering serum total or LDL cholesterol levels or increasing serum HDL cholesterol levels.

The invention also provides a pharmaceutical composition for use in lowering serum total or LDL cholesterol levels or increasing serum HDL cholesterol levels comprising an effective amount of Z-2-[4-(4-chloro-1,2-diphenyl-but-1-enyl)phenoxy]ethanol.

The invention also provides the use of Z-2-[4-(4chloro-1,2-diphenyl-but-1-enyl)phenoxy]ethanol in the manufacture of a medicament for the prevention or treatment of atherosclerosis.

The compound of the invention may be administered in a variety of ways including orally, parenterally or transdermally using conventional forms of preparations, such as capsules, tablets, granules, powders, suppositories, injections, patches, suspensions and syrups. The term "effective amount" means an amount of compound of the invention which is capable of lowering serum total or LDL cholesterol levels or increasing serum HDL cholesterol levels. The compound of the invention may be administered according to the method of the invention monthly, weekly or daily or several times a day depending upon the patent's needs. A typical daily oral dosage is within the range of from about 0.5 mg to about 1000 mg, preferably from about 10 mg to about 800 mg, of the active compound. However, the dosage may be properly varied depending on the age, body weight and conditions of the patient as well as on the administration method. The compound of the invention may be administered alone or together with other active compounds.

The compositions according to the invention can be prepared by the methods commonly employed in the art. In addition to the active compound the compositions may contain pharmaceutically acceptable additives commonly used in the art, such as carriers, binders, excipients, lubricants, suspending agents and diluents. The amount of the active compound in the compositions of the invention is sufficient to produce the desired therapeutical effect, for example about 0.5 to 1000 mg, preferably about 10 mg to 800 mg, in unit dosage for both oral and parenteral administration.

The following examples illustrate the synthesis of the compound of the invention.

EXAMPLES

Example 1

Z-2-[4-(4-chloro-1,2-diphenyl-but-1-enyl)phenoxy]ethanol
(i) Z-4-[4-(2-benzyloxyethoxy)-phenyl]-3,4-diphenyl-but-3-en-1-ol The reaction vessel was charged with toluene (790 ml), 48% aqueous sodium hydroxide (790 ml), tetrabutylammonium bromide (2.12 g, 6.6 mmol) and Z-4-(4-hydroxy-1,2-diphenyl-but-1-enyl)-phenol (50 g, 0.16 mol) prepared by the method described by U.S. Pat. No. 4,996,225. The mixture was refluxed for 30 minutes. Benzyl-(2-bromoethyl) ether (Grobelny D. et al., Tetrahedron Letters 28, 2639–42, 1979) (41.7 g, 0.19 mol) was added to the reaction mixture and the refluxing was continued for 2 hours. Then the mixture was cooled to room temperature, layers were separated and aqueous phase was washed with toluene. Toluene phases were combined, washed with water, dried and evaporated to dryness. The residue was used in the next stage without further purification.

$^1$H NMR (300 MHz, CDCl$_3$): d 1.2 (1H, t, OH), 2.8 (2H, t, CH$_2$—C=), 3.6 (2H, dt, CH$_2$OH), 3.7 (2H, t, CH$_2$OBn), 4.0 (2H, t, CH$_2$OPh), 4.6 (2H, s, OCH$_2$Ph), 6.6 (2H, d, H-PhO), 6.8 (2H, d, H-PhO), 7.1–7.4 (15H, m, H-Ph).

(ii) Z-1-[4-(2-benzyloxyethoxy)-phenyl]-4-chloro-1,2-diphenyl-but-1-ene

Z-4-[4-(2-benzyloxyethoxy)-phenyl]-3,4-diphenyl-but-3-en-1-ol prepared in the previous stage was dissolved in acetonitrile (400 ml). Triphenyl phosphine (103.5 g, 0.4 mol) and tetrachloromethane (120 g, 0.79 mol) were added and the mixture was refluxed for 2 hours. Then the mixture was evaporated to dryness under reduced pressure. The residue was dissolved in methanol (160 ml) and water (40 ml) and extracted three times with petroleum ether (3×200 ml) at boiling point. Petroleum ether layers were combined and evaporated to dryness under reduced pressure. The residue was crystallized twice from ethanol (700 ml). Yield 36 g.

$^1$H NMR (300 MHz, CDCl$_3$): d 2.9 (2H, t, CH$_2$—C=), 3.4 (2H, dt, CH$_2$Cl), 3.7 (2H, t, CH$_2$OBn), 4.0 (2H, t, CH$_2$OPh), 4.6 (2H, s, OCH$_2$Ph), 6.6 (2H, d, H-PhO), 6.8 (2H, d, H-PhO), 7.1–7.4 (15H, m, H-Ph).

(iii) Z-2-[4-(4-chloro-1,2-diphenyl-but-1-enyl)-phenoxy]-ethanol

Z-1-[4-(2-benzyloxyethoxy)-phenyl]-4-chloro-1,2-diphenyl-but-1-ene (36 g, 0.08 mol) was dissolved in the mixture of ethyl acetate (350 ml) and ethanol (350 ml). Palladium on carbon (5%, 0.28 g) was added and the solution was flushed with hydrogen gas until there was not any starting compound left (thin layer chromatography). Palladium on carbon was filtered off through siliceous earth and the filtrate was evaporated. The residue was crystallized from the mixture of ethanol (155 ml) and water (65 ml). Yield 20 g.

$^1$H NMR (300 MHz, CDCl$_3$): d 2.9 (2H, t, CH$_2$—C=), 3.4 (2H, dt, CH$_2$Cl), 3.84–3.89 (2H, m, CH$_2$OH), 3.92–3.96 (2H, m, CH$_2$OPh), 6.6 (2H, d, H-PhO), 6.8 (2H, d, H-PhO), 7.1–7.4 (10H, m, H-Ph).

The effect of Z-2-[4-(4-chloro-1,2-diphenyl-but-1-enyl) phenoxy]ethanol in lowering serum cholesterol levels is demonstrated by the following experiments.

EXPERIMENTS

In vivo study in rats

In this study adult female Spraque-Dawley rats were used. The compound of the invention was dissolved into vehicle (148 mM NaCl, 2.9% Magrocol 3000, 0.19% Tween 20) at different concentrations (0.5–10 mg/ml). The animals were dosed once daily with the solutions (1 ml/kg) by oral gavage for 28 days. The control animals received mere vehicle. The final daily doses of the compound of the invention were 0, 0.5, 1, 5 or 10 mg/kg. At the end of the treatment period blood samples were collected by heart puncture from anesthetized animals. The separated serum samples were analyzed for cholesterol, cholesterol precursor molecules and selected phytosterols by gas chromatography (Miettinen T., J. Lipid. Res. 29, 43–51, 1988).

The results are shown in Table 1. The test compound decreased serum total cholesterol level by 34% at the highest dose level. The relative phytosterol content also decreased slightly at the highest dose level (e.g. β-sitosterol level by 20%, Table 1). There was no significant changes in serum squalene or precursor sterol content, except in the relative lathosterol content that increased by about 50% (Table 1).

A preliminary data from a 3-month rat study supports the concept that Z-2-[4-(4-chloro-1,2-diphenyl-but-1-enyl) phenoxy]ethanol is a potent serum cholesterol lowering agent: daily dose of 0.5 or 2 mg/kg decreased serum total cholesterol level by 15–25 or 30–40%, respectively.

TABLE 1

Effect on serum total cholesterol, lathosterol and b-sitosterol content in female rat after 4 weeks oral administration. The values (mean ± SEM) are indicated as percent of the control values

| Dose (mg/kg) | Cholesterol | Lathosterol[a] | β-Sitosterol[a] |
|---|---|---|---|
| 0.5 | 90.7 ± 8.4 | 78.3 ± 2.3 | 106.0 ± 7.6 |
| 1 | 91.1 ± 5.0 | 87.2 ± 10.3 | 90.6 ± 6.4 |
| 5 | 89.0 ± 7.5 | 80.1 ± 16.8 | 90.9 ± 6.5 |
| 10 | 65.7 ± 7.0* | 146.6 ± 14.74 | 79.6 ± 1.0* |

[a]Values relative to the cholesterol content
* = 2p < 0.05

Cholesterol biosynthesis study

The effects on cholesterol biosynthesis were also studied in vitro in Hep G2 cell cultures using $^{14}$C-acetate as cholesterol precursor. The test compound was added into the culture medium at concentrations from 0.001 to 5 micromolar. After 2 hours the the culture was stopped and the newly synthetized cholesterol was quantitated by thin-layer chromatography.

In the in vitro cell culture system used the test compound did not inhibit cholesterol biosynthesis directly.

Phase I clinical study

In a phase I clinical double blind study the test compound was given perorally to healthy postmenopausal women daily for 12 weeks followed by a 2-weeks recovery period (10 subjects at each dose level). The doses used were 25, 50, 100 and 200 mg and serum lipide values were analyzed at 2 weeks intervals. Serum total cholesterol and HDL cholesterol content was determined by an enzymatic PAP-method, HDL cholesterol after PEG-precipitation. LDL-cholesterol values were calculated.

In the phase I clinical study at the dose level 200 mg the serum total cholesterol level decreased significantly (p<0.02) from 2 weeks onwards and the maximal decrease was about 12% from the baseline. The decrease in serum LDL level was even more pronouced (p<0.003): the decrease was maximally 22% from the baseline (dose level 200 mg). The test compound tended also increase HDL-cholesterol level, the increase was significant at the 200 mg dose level (an 10% increase over baseline, p<0.04). The serum HDL/LDL cholesterol ratio tended to increase and this increase was highly significant (p<0.0001) at the 200 mg dose level. During the recovery period the lipide values returned to the baseline level. No significant changes were seen in the placebo group.

Discussion

The mechanism by which the test compound decreases serum cholesterol content can be either direct inhibition of cholesterol biosynthesis, an effect on serum lipoprotein metabolism or an effect on cholesterol absorption from the gut, or some combination of these mechanisms. According to the present data a direct biosynthesis inhibition seems unlikely. A direct biosynthesis inhibition is not strong at the post-squalene stages of the pathway as the accumulation of precursor sterols is minimal at the doses studied. The decrease in β-sitosterol level may indicate that cholesterol absorption is slightly impaired.

The human data suggests that Z-2-[4-(4-chloro-1,2-diphenyl-but-1-enyl)phenoxy]ethanol has beneficial lipid effects in clinical use: the cholesterol levels and especially harmful LDL-cholesterol level decrease markedly. In addition, an increase in the protective HDL-cholesterol level was noticed. In summary, the test compound is likely to inhibit or slow down the process of atherosclerosis in clinical use. The precise mechanism of action of the compound is to be elucidated with further experimentation.

We claim:

1. A method of lowering serum total and LDL cholesterol levels and increasing serum HDL cholesterol levels in a subject in need of said cholesterol method, which comprises administering an effective amount of Z-2-[4-(4-chloro-1,2-diphenyl-but-1-enyl)phenoxy]ethanol to said subject.

2. A method for preventing or treating atherosclerosis in a subject in need of said treatment or prevention, which method comprises administering an effective amount of Z-2-[4-(4-chloro-1,2-diphenyl-but-1-enyl)phenoxy]ethanol to said subject.

3. A method of lowering the serum total cholesterol level in a subject in need of said lowering, which method comprises administering and effective amount of Z-2-[4-(4-chloro-1,2-diphenyl-but-1-enyl)phenoxy]ethanol to said subject.

4. A method of lowering the serum LDL cholesterol level in a subject in need of said lowering, which method comprises administering an effective amount of Z-2-[4-(4-chloro-1,2-diphenyl-but-1-enyl)phenoxy]ethanol to said subject.

5. A method of increasing the serum HDL cholesterol level in a subject in need of said increase, which method comprises administering an effective amount of Z-2-[4-(4-chloro-1,2-diphenyl-but-1-enyl)phenoxy]ethanol to said subject.

6. A method of increasing the serum HDL/LDL cholesterol ratio in a subject in need of said increase, which method comprises administering an effective amount of Z-2-[4-(4-chloro-1,2-diphenyl-but-1-enyl)phenoxy]ethanol to said subject.

* * * * *